(12) United States Patent
Kurtzer et al.

(10) Patent No.: US 6,923,801 B2
(45) Date of Patent: Aug. 2, 2005

(54) ABLATION DEVICE PLACEMENT SPACER

(75) Inventors: Jeffrey D. Kurtzer, San Clemente, CA (US); Sanford D. Damasco, Irvine, CA (US)

(73) Assignee: Endocare, Inc., Irvine, CA (US)

( * ) Notice: Subject to any disclaimer, the term of this patent is extended or adjusted under 35 U.S.C. 154(b) by 0 days.

(21) Appl. No.: 10/659,876

(22) Filed: Sep. 11, 2003

(65) Prior Publication Data

US 2005/0059961 A1 Mar. 17, 2005

(51) Int. Cl.[7] .............................................. A61B 17/00
(52) U.S. Cl. ............................... 606/1; 606/32; 606/41
(58) Field of Search ............................... 606/1, 13, 34, 606/41, 130; 604/116–118; 600/429, 461

(56) References Cited

U.S. PATENT DOCUMENTS

| 5,868,673 A | 2/1999 | Vesely |
| 5,961,527 A | 10/1999 | Whitmore |
| 6,010,446 A | 1/2000 | Grimm |
| 6,036,632 A | 3/2000 | Whitmore |
| 6,206,832 B1 | 3/2001 | Downey |
| 6,554,759 B2 | 4/2003 | Fontayne |
| 6,572,525 B1 | 6/2003 | Yoshizumi |

*Primary Examiner*—Rosiland Rollins
(74) *Attorney, Agent, or Firm*—Lawrence N. Ginsberg

(57) ABSTRACT

An ablation device placement spacer for use with a patient undergoing a targeted ablation procedure utilizing elongated ablation devices insertable into treatment zones of the patient. The ablation device placement spacer includes an elongated spacing member and at least one ablation device engaging element positioned on the elongated spacing member. During use, an ablation device is releasably engageable with the ablation device engaging element, a spacing portion of the elongated spacing member being spaced from the ablation device engaging element at a desired distance so as to provide the user with an indication of a desired spacing for a subsequent ablation device to be inserted into its respect treatment zone.

14 Claims, 2 Drawing Sheets

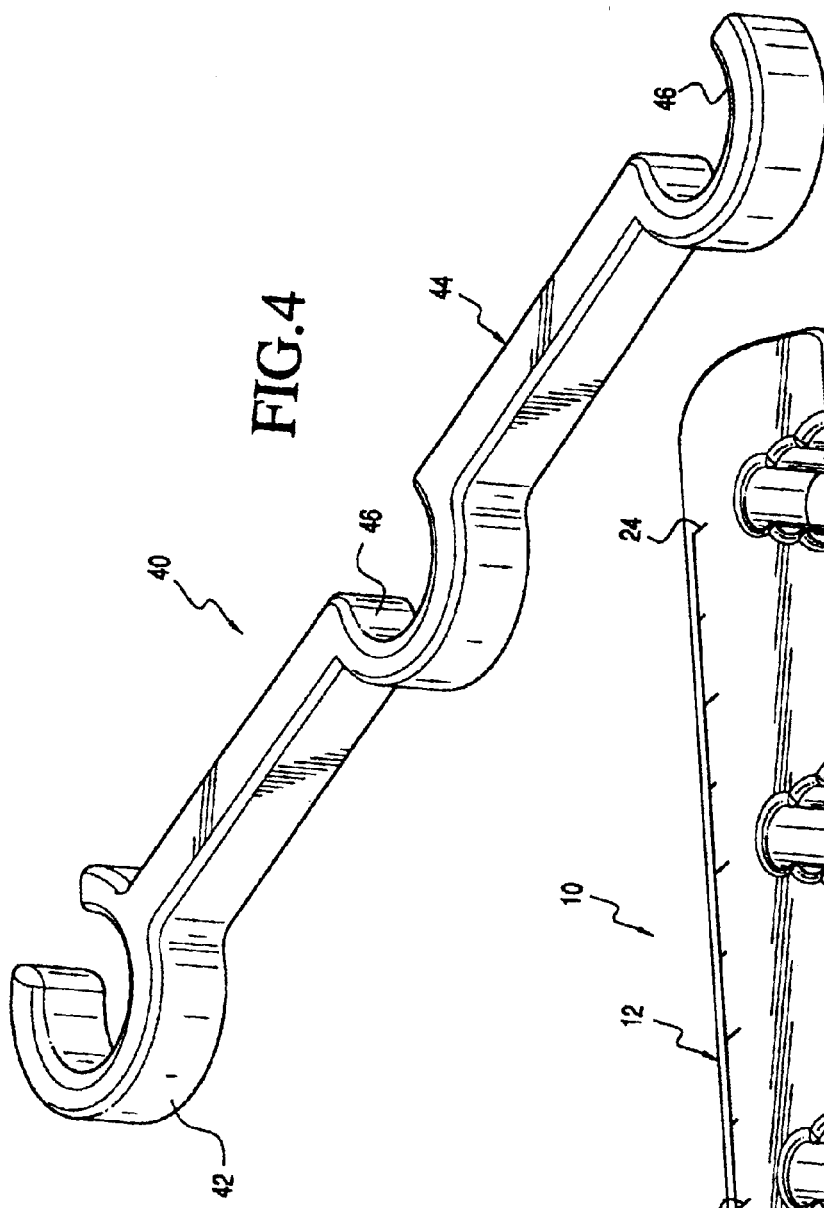

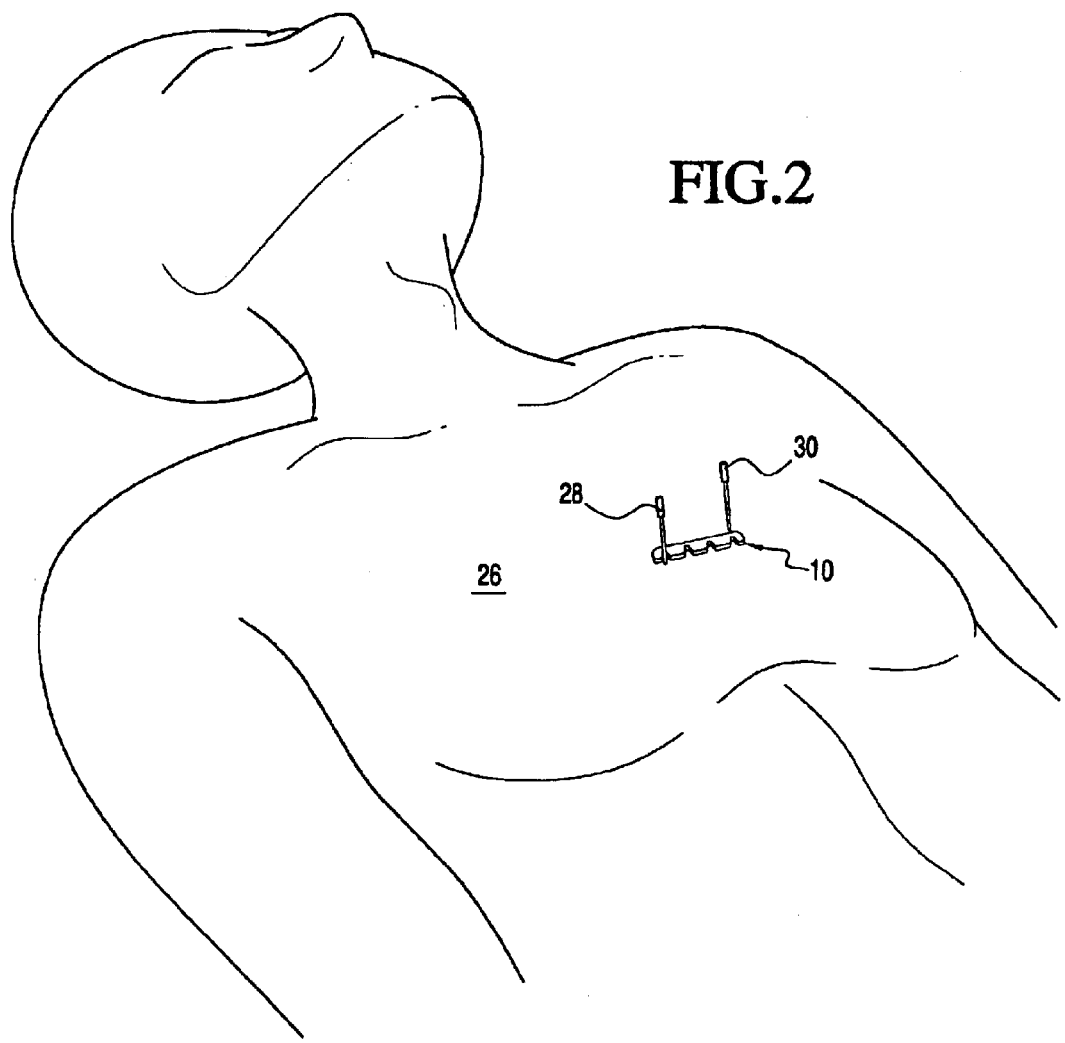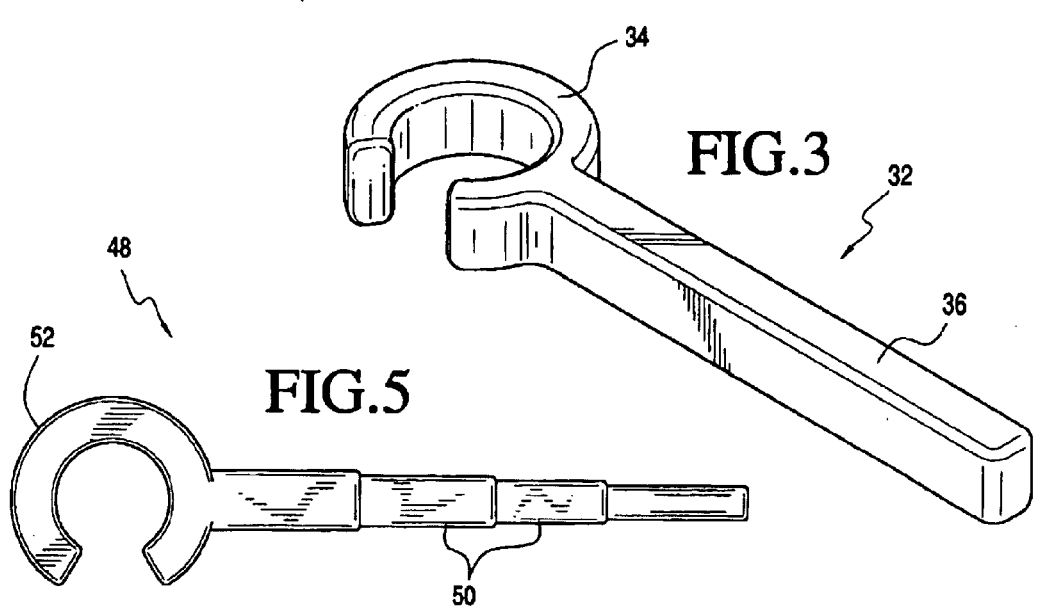

ABLATION DEVICE PLACEMENT SPACER

BACKGROUND OF THE INVENTION

1. Field of the Invention

The present invention relates to ablation device placement during targeted ablation and more particularly to a spacer for establishing the spacing between ablation devices during such ablation procedures.

2. Description of the Related Art

Cryosurgical probes are used to destroy living tissue by thermally manipulating a cryoprobe to extreme temperatures by using freezing and heating cycles. Similarly, other ablative devices such as RF probes are used to ablate the tissue. Currently cryosurgical probes are incorporated into computer guided cryosurgery systems wherein the systems calculate the optimal placement for the cryoprobes into diseased tissue. Entry position grids are typically utilized for aiding the user in locating the approximate entry point of cryoprobe into the patient during a cryosurgical procedure. U.S. Pat. No. 6,036,632, issued to W. F. Whitmore III, for example, discloses an example of a sterile disposable template grid system for positioning and implanting medical implants.

However, there are certain deficiencies with respect to the use of such entry position grids. These grids define fixed patterns for probe placement and therefore restrict the user to a limited number of insertion distances. As a result, anatomy is not accounted for such as adjacent organs, blood vessels and bone.

There is a need to provide greater flexibility in spacing ablation devices so as to be commensurate with recent improvements in computer guided cryosurgery systems.

SUMMARY OF THE INVENTION

In one broad aspect, the present invention is an ablation device placement spacer for use with a patient undergoing a targeted ablation procedure utilizing elongated ablation devices insertable into treatment zones of the patient. The ablation device placement spacer includes an elongated spacing member and at least one ablation device engaging element positioned on the elongated spacing member. During use, an ablation device is releasably engageable with the ablation device engaging element, a spacing portion of the elongated spacing member being spaced from the ablation device engaging element at a desired distance so as to provide the user with an indication of a desired spacing for a subsequent ablation device to be inserted into its respect treatment zone.

Preferably, the elongated spacing member includes a plurality of spaced openings formed along a side edge thereof. The openings function as the ablation device engaging elements.

As opposed to placing additional probes only based on visual guidance (using CT, MRI, ultrasound or other visual imaging means) the present invention provides enhanced placement distances to optimize the treatment.

Fixed grids provide preset orientation and distance parameters between ablation devices. The present invention, on the other hand, is not orientation dependent while still providing optimal distance parameters. Use of the present invention with its engaging element minimizes handling requirements during the placement of additional ablation devices.

BRIEF DESCRIPTION OF THE DRAWINGS

FIG. 1 is a perspective view of a first embodiment of the ablation device placement spacer of the present invention having spaced openings along a side edge of an elongated spacing member.

FIG. 2 is a schematic perspective view of an upper torso of a patient showing an ablation device placement spacer being used to position an ablation device.

FIG. 3 is a perspective view of a second embodiment of the ablation device placement spacer that has a single arcuate engaging element located at an end of the elongated spacing member.

FIG. 4 is a perspective view of another embodiment of the ablation device placement spacer that has an arcuate engaging element located at an end of the elongated spacing member and spaced openings formed along a side edge thereof.

FIG. 5 is a perspective view of another embodiment of the ablation device placement spacer that utilizes telescoping elements.

DETAILED DESCRIPTION OF THE INVENTION

Referring now to the drawings and the characters of reference marked thereon, FIG. 1 illustrates a preferred embodiment of the ablation device placement spacer of the present invention, designated generally as 10. The ablation device placement spacer 10 includes an elongated spacing member 12 and ablation device engaging elements 14, i.e. spaced openings or recesses, formed along a side edge 16 thereof.

Each recess 14 is preferably formed of relatively large arcuate surfaces 18 for accommodating a relatively large diameter ablation device and progressively smaller arcuate surfaces 20, 22 formed in the relatively large arcuate surfaces 18 for accommodating progressively smaller diameter ablation devices. Surfaces 18, 20, 22 are arcuate so as to provide a complementary fit with an outer surface of an ablation device, which typically has a circular cross-section. They may be sufficiently closed to provide a snap fit with an ablation device. Or, the releasable engagement may be very loose, i.e. merely an abutting engagement.

The elongated spacing member 12 preferably includes measuring indicia 24 for indicating the distance from an ablation device to a subsequent ablation device to be inserted. The elongated spacing member 12 is preferably formed of a rigid plastic; however, it may be formed of other suitable materials such as metal, etc.

Referring now to FIG. 2, utilization of the ablation device placement spacer 10 with a patient 26 is illustrated. During use, a first ablation device 28 is introduced into a treatment zone of the patient 26. An end recess of the ablation device placement spacer 10 is then engaged with the ablation device 28. The ablation device placement spacer 10 can be rotated about the ablation device 28 to provide the desired relative angle for locating a subsequent ablation device 30. The subsequent ablation device 30 can be distanced from the first device 28 as desired.

The placement spacer 10 is particularly adapted for use with ablation devices such as cryosurgical probes or RF probes. Additionally, the ablation device may include components such as temperature sensors that may use the present placement spacer. Present assignee, Endocare, Inc. of Irvine, Calif. manufactures and markets a cryosurgical system under the trademark CryoCare® including its newly enhanced automated feedback, marketed under the trademark AutoFreeze™. The CryoCare® surgical system® provides a treatment guidance plan for placing the ablative devices. Guidance as to recommended ablative element placement within a prostate is provided based on images of the prostate acquired from an imaging system, such as an ultrasound system.

The openings 18, 20, 22 provided allow for differing ablative device diameters. For example, for typical cryosurgical probes, openings may be 1.5 mm, 2.4 mm and 3.4 mm in diameter.

The present ablative element placement spacer 10 is useful in various types of surgeries, including open surgery, endoscopic surgery and percutaneous surgery.

Referring now to FIG. 3 another embodiment of the ablation device placement spacer is illustrated, designated generally as 32. In this embodiment the spacer includes a single arcuate engaging element 34 located at an end of the elongated spacing member 36. Different length spacers 32 may be provided depending on the desired distance between ablation devices. As in the previous embodiment the engaging element may be designed to provide a snap fit.

Referring now to FIG. 4 another embodiment of the ablation device placement spacer is illustrated, designated generally as 40. In this embodiment the spacer 40 includes an arcuate engaging element which comprises a snapping element 42 located at an end of the elongated spacing member 44. The elongated element 44 has spaced openings 46 formed thereon for placement of subsequent ablation devices.

Referring now to FIG. 5, another embodiment of the ablation device placement spacer is illustrated, designated generally as 48. In this embodiment the elongated spacing member includes telescoping elements 50 that provide a desired length. An ablation device engaging element 52 is located at the end of the elongated spacing member. There are numerous ways in which the telescoping elements 50 can be made to cooperate, as well known to those skilled in the art.

Other embodiments and configurations may be devised without departing from the spirit of the invention and the scope of the appended claims.

What is claimed is:

1. An ablation device placement spacer for use with a patient undergoing a targeted ablation procedure utilizing elongated ablation devices insertable into treatment zones of the patient, comprising:
    an elongated spacing member; and,
    at least one ablation device engaging element positioned on said elongated spacing member defined by an opening formed along a side edge of said elongated spacing member, wherein during use an ablation device is releasably engageable with said ablation device engaging element, a spacing portion of said elongated spacing member being spaced from said ablation device engaging element at a desired distance so as to provide the user with an indication of a desired spacing for a subsequent ablation device to be inserted into its respect treatment zone,
    wherein said at least one ablation device engaging element is arcuate to provide a complementary fit with a circular outer surface of said ablation device, and further wherein said engaging element is capable of being rotated about said ablation device to provide a circular path having a desired radius for placement of a subsequent ablation device.

2. The ablation device placement spacer of claim 1, wherein said elongated spacing member, comprises a plurality of said ablation device engaging elements defined by a plurality of said spaced openings formed along said side edge thereof.

3. The ablation device placement spacer of claim 1, wherein said elongated spacing member, comprises:
    a plurality of said ablation device engaging elements defined by a plurality of said spaced openings formed along a said side edge thereof, each of said plurality of spaced openings being defined by relatively large arcuate surfaces for accommodating a relatively large diameter ablation device and at least one progressively smaller arcuate surface formed in said relatively large arcuate surface for accommodating progressively smaller diameter ablation devices.

4. The ablation device placement spacer of claim 1, wherein said at least one ablation device engaging element comprises a single arcuate engaging element located at an end of said elongated spacing member.

5. The ablation device placement spacer of claim 1, wherein said at least one ablation device engaging element comprises a single arcuate engaging element located at an end of said elongated spacing member, said single arcuate engaging element providing a snap fit with an ablation device.

6. The ablation device placement spacer of claim 1, wherein said at least one ablation device engaging element comprises an arcuate element located at an end of said elongated spacing member, said elongated spacing member comprising a plurality of spaced openings formed thereon.

7. The ablation device placement spacer of claim 1, wherein said at least one ablation device engaging element comprises an arcuate snapping element located at an end of said elongated spacing member, said elongated spacing member comprising a plurality of spaced openings formed thereon.

8. The ablation device placement spacer of claim 1, wherein said elongated spacing member comprises a plurality of telescoping elements.

9. The ablation device placement spacer of claim 1, wherein said elongated spacing member comprises measuring indicia for indicating the distance from an ablation device to a subsequent ablation device to be inserted.

10. The ablation device placement spacer of claim 1, wherein said at least one ablation device engaging element is so constructed and arranged to accommodate a cryosurgical probe.

11. A method for providing ablative surgical treatment of a patient, comprising the steps of:
    a) introducing a first ablation device into a treatment zone of a patient;
    b) releasably engaging an ablation device placement spacer with said first ablation device, said ablation device placement spacer, comprising:
        i. an elongated spacing member; and,
        ii. at least one ablation device engaging element positioned on said elongated spacing member, a spacing portion of said elongated spacing member being spaced from said ablation device engaging element at a desired distance so as to provide the user with an indication of a desired spacing for a subsequent ablation device to be inserted into its respect treatment zone, wherein said at least one ablation device engaging element is arcuate to provide a complementary fit with a circular outer surface of said ablation device, wherein said engaging element is capable of being rotated about said ablation device to provide a circular path having a desired radius for placement of a subsequent ablation device; and,
    c) introducing a subsequent ablation device at said desired distance.

12. The method of claim 11, wherein said steps of introducing first and subsequent ablation devices are performed in open surgery.

13. The method of claim 11, wherein said steps of introducing first and subsequent ablation devices are performed in endoscopic surgery.

14. The method of claim 11, wherein said steps of introducing first and subsequent ablation devices are performed in percutaneous surgery.

* * * * *